(12) United States Patent
Claudon

(10) Patent No.: US 9,383,305 B2
(45) Date of Patent: Jul. 5, 2016

(54) METHOD AND SYSTEM FOR CONTROLLING A FILTER

(75) Inventor: Philippe Claudon, Belfort (FR)

(73) Assignee: GE Energy Products France SNC, Belfort (FR)

( * ) Notice: Subject to any disclaimer, the term of this patent is extended or adjusted under 35 U.S.C. 154(b) by 290 days.

(21) Appl. No.: 13/823,020

(22) PCT Filed: Sep. 12, 2011

(86) PCT No.: PCT/EP2011/065747
§ 371 (c)(1),
(2), (4) Date: Jul. 9, 2013

(87) PCT Pub. No.: WO2012/034971
PCT Pub. Date: Mar. 22, 2012

(65) Prior Publication Data
US 2013/0276514 A1    Oct. 24, 2013

(30) Foreign Application Priority Data

Sep. 13, 2010 (FR) ...................... 10 57254

(51) Int. Cl.
*G01N 15/08* (2006.01)
*B01D 46/44* (2006.01)
(52) U.S. Cl.
CPC ............... *G01N 15/08* (2013.01); *B01D 46/442* (2013.01); *B01D 46/444* (2013.01); *B01D 46/446* (2013.01); *F05B 2260/80* (2013.01); *G01N 2015/084* (2013.01)

(58) Field of Classification Search
CPC .................................. G01N 2015/084
See application file for complete search history.

(56) References Cited

U.S. PATENT DOCUMENTS

| 4,494,403 A * | 1/1985 | Bowers et al. ............. 73/40.7 |
| 2004/0055900 A1 * | 3/2004 | Smeltzer et al. .......... 205/784.5 |
| 2009/0266048 A1 * | 10/2009 | Schwarz .................. 60/39.092 |
| 2011/0048228 A1 * | 3/2011 | Handley et al. ............... 95/45 |

FOREIGN PATENT DOCUMENTS

| DE | 295 07 061 | 7/1995 |
| DE | 299 07 077 | 7/2000 |

OTHER PUBLICATIONS

International Search Report for PCT/EP2011/065747, Oct. 21, 2011 (2 pages).
Written Opinion for PCT/EP2011/065747, Oct. 21, 2011, 8 pages.
PDHengineer.com: "Filters for Industry," Chapter 3, Jan. 1, 2002, pp. 1-42, XP007918177, retrieved from: <www.pdhengineer.com/courses/hv/m_4009.pdf>.

* cited by examiner

*Primary Examiner* — Paul West
(74) *Attorney, Agent, or Firm* — Mintz Levin Cohn Ferris Glovsky and Popeo, P.C.; Steven M. Jensen

(57) ABSTRACT

According to the method for controlling a filter (3) for an air intake duct of a turbine: the filter (3) is exposed to an incident flow of sprayed salt water; and parameters of the flow on either side of the filter, which are representative of the salt retention capability of the filter, are measured.

10 Claims, 1 Drawing Sheet

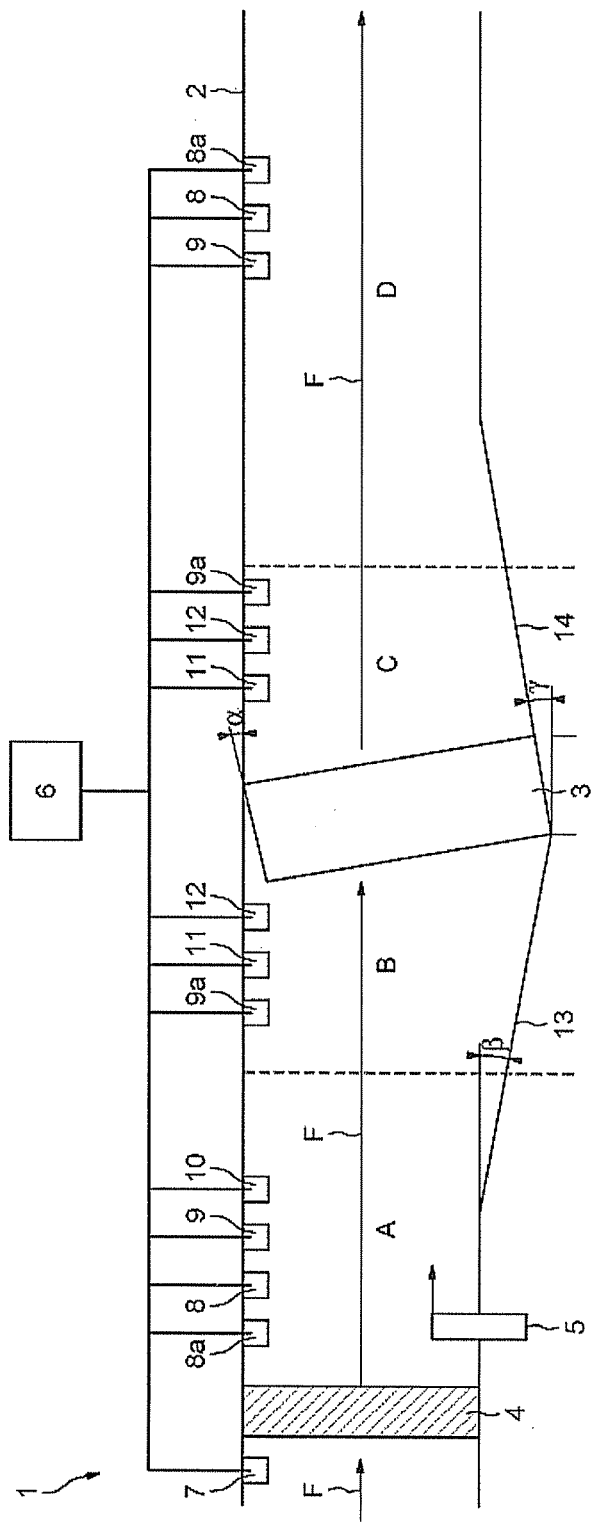

METHOD AND SYSTEM FOR CONTROLLING A FILTER

RELATED APPLICATION DATA

This application is the U.S. national phase, pursuant to 35 U.S.C. §371, of international application Ser. No. PCT/EP2011/065747, filed Sep. 12, 2011, designating the United States and published in French on Mar. 22, 2012 as publication No. WO 2012/034971 A1, which claims priority to French application Ser. No. 1057254, filed Sep. 13, 2010. The entire contents of the aforementioned patent applications are incorporated herein by this reference.

The invention relates to the filters for air intake ducts in a turbine, in particular a gas turbine.

More particularly, the invention relates to the filters used in installations situated in a salt water-rich environment.

As is known, the air contains fine particles of dust, most of which are of the order of a few microns. In as much as it sucks in a considerable quantity of air, a turbine is very sensitive to the negative effects of these dust particles.

The atmospheric air can contain dust, mist, rain water, salt water, carbon particles, etc. Consequently, the air sucked in by the turbine is likely to cause corrosion and pollution inside the duct of the turbine and in particular inside the air compressor which is located first in the duct. The performance of the compressor is reduced, thus generating a reduction in the efficiency of the power generator of the turbine.

In order to reduce these risks, a filter is generally placed at the inlet of the air intake duct of the turbine, so as to avoid the deposition of dust particles contained in the air in the compressor of the turbine.

For this, it is important to monitor the filters used well in order for them to be able to filter a maximum of residues present in the atmosphere and in particular the salt present in sea water.

Improving the performance levels of the filters makes it possible to reduce the turbine shutdowns, extend their life and increase their efficiency.

There are various main filtration effectiveness tests. One parameter which makes it possible to monitor the filtration effectiveness is the retention of the filter. The retention corresponds to the ratio between the weight of the dust particles retained and the overall weight of the dust exposed to the filter. The dust trace corresponding to the relative visual clogging characteristics due to the dust which has passed through the filter can also be considered.

The objective of the invention is therefore to provide a method and a system for monitoring the performance levels of filters for air intake ducts of a turbine.

In one embodiment, the invention relates to a method for monitoring a filter for an air intake duct of a turbine in which the filter is subject to an incident flow of sprayed salt water, and parameters of the flow on either side of the filter, representative of the salt retention capability of the filter, are measured. Thus, it is possible to determine the performance levels of a filter present in a maritime environment.

However, there is no departure from the invention when the filter to be monitored is used in an environment other than the maritime environment.

Advantageously, the measurement steps are carried out in a sequence of at least one test.

For example, on each test, measurement members are moved in a test duct in which the filter is placed.

Three fifteen-minute tests can be performed, at twenty-minute intervals.

Furthermore, four test sequences are performed.

The filter can advantageously be dried between the sequences.

Advantageously, the filter is inclined by ten degrees relative to the horizontal axis.

For example, each test comprises the measurement of the salt concentration, of the salt water droplet distribution and of the quantity of water and of salt.

The dry filter can be charged with dust and at least one test sequence can be performed on the dry filter charged with dust.

For example, the salt retention capability of the filter is measured.

According to a second aspect, the invention relates to a system for monitoring a filter for an air intake duct in a turbine comprising a means for injecting a flow of sprayed salt water toward the filter.

The monitoring system also comprises members for measuring parameters of the flow on either side of the filter representative of the salt retention capability of the filter.

For example, the measurement members comprise at least one member chosen from a flow meter, a conductivity meter, a photometer, a white light spectrometer, a humidity sensor, a pressure sensor and a particle measurement device.

Other aims, features and advantages of the invention will become apparent on reading the following description, given solely as a non-limiting example, and with reference to the appended drawing which illustrates a system for monitoring a filter in a test duct according to the invention.

As illustrated in the appended FIGURE, the monitoring system 1 comprises a test duct 2 in which a filter to be tested 3 is mounted and in which test steps are carried out to determine the salt retention capability of the filters 3. The test duct 2 is thus provided with an appropriate support for the filter 3 (not represented) in order to position it transversally in the duct in the path of an incident air flow illustrated by arrows F.

A high performance filter 4, called "HEPA" filter, is mounted at the inlet of the test duct 2 so as to supply quality air in the duct, in particular in different measurement areas A, B, C and D. The measurement area A is situated between the HEPA filter 4 and the filter to be tested 3 as far as the area B which is situated directly upstream of the filter 3. The area C is situated directly downstream of the filter 3 and the area D is situated downstream of the area C. The test duct 2 comprises a means 5 for injecting a flow of salt water toward the filter 3 and an air transmission device (not represented) situated upstream of the test duct 2.

The monitoring system 1 comprises members for measuring parameters of the flow arranged on either side of the filter 3. These measurement members are linked to a computer 6 which makes it possible to record the measurements performed. The measurement members comprise, for example, a flow meter 7, a humidity sensor 8, a static pressure sensor 8a, a white light spectrometer 9, a graduated means 9a, a photometer 10, a conductivity meter 11 and a means 12 for measuring the number of particles. Obviously, one or more of these members can be used depending on the types of test to be carried out. Other types of measurement members can also be used.

The flow meter 7 is situated upstream of the HEPA filter 4 and makes it possible to determine the flow rate of the incoming air. A humidity sensor 8 and a static pressure sensor 8a are situated in each of the areas A and D. The white light spectrometer 9 and makes it possible to determine the quantity of water in the area A injected by the injection means 5 and the quantity of water in the area D. The graduated means 9a is situated in the areas B and C and makes it possible to determine the quantity of water present in these areas. The photometer 10 is situated in the area A and makes it possible to determine the salt concentration. The conductivity meter 11 and the means 12 for measuring the number of particles are situated in the areas B and C on either side of the filter 3. The conductivity meter 11 determines the salt concentration and the measurement means 12 makes it possible to determine the partial effectiveness of the filter 3. The partial effectiveness corresponds to the number of particles situated downstream of the filter 3 compared to the number of particles of the same size situated upstream of the filter 3.

The duct 2 as represented has, by way of non-limiting example, a stepped form so as to obtain a better distribution of the injection of the salt wafer on the filter 3. A first level difference 13 forms an angle β with the horizontal axis, then a second level difference 14 forms an angle γ with the horizontal axis. The angle β can be less than 7° and the angle γ can be greater than 20°. A duct that is straight or with different angles β and γ can also be considered to perform the monitoring of the filter 3.

The filter 3 to be tested is inclined by an angle α relative to the horizontal axis of the duct 2. The angle α can be 10°. The filter 3 is mounted in the duct 2 by seal-tight fastening means (not represented) in order to direct the flow of salt water only through the filter 3.

The salt concentration injected by the injection means 5 can be, for example, 35 g/L.

A first monitoring step consists in calibrating the white light spectrometer 9 and the means 12 for measuring the number of particles. During this first step, the filter to be tested 3 is not positioned in the duct 2. A flow of air is directed by the air transmission device through the HEPA filter 4 so as to obtain a good air quality in the measurement areas A, B, C and D, then the salt water is injected by the injection means 5. The flow of air makes it possible to obtain an incident flow of sprayed salt water toward the filter 3.

The computer 6 records the values from the white light spectrometer 9, from the conductivity meter 11 and from the means 12 for measuring the number of particles upstream and downstream of the HEPA filter 4, that is to say, respectively, the values of the quantity of water, of the salt concentration and of the number of particles.

A second step consists in inserting and locking the filter 3 in the duct 2, then the flow of air is transmitted by the air transmission device and the filter 3 is subjected to the incident flow of sprayed salt water by the injection means 5 for a determined duration, for example three hours.

A third step consists in carrying out three tests during one hour. Each test comprises the measurement of the quantity of water by the white light spectrometer 9, the measurement of the salt concentration by the photometer 10 and the measurement of the number of particles by the measurement means 12 in order to determine the partial effectiveness of the filter 3.

Each test lasts approximately fifteen minutes. There is an interval of approximately twenty minutes between each test start. After each test, the white light spectrometer 9 and the photometer 10 are moved in the duct 2 along the horizontal axis. During the tests, the measurement members 9 and 10 can be positioned in the area B, then in the area A, then in the area D.

During a fourth step, the three tests are repeated for approximately two hours, in order to obtain three measurements from each of the measurement members 9, 10 and 12 and deduce an average therefrom.

The steps 1 to 4 are subsequently called "test sequences".

The fifth step consists in drying the filter 3, for example by increasing the flow rate of the air. The filter is dried for approximately twelve hours then its humidity rate is checked. When the filter 3 is dry, the test sequence is repeated at least once. The test sequence can be repeated up to four times.

When the fifth step is finished, the dry filter 3 is charged with dust at 450 Pa, for example of ASHRAE type, and the test sequence is repeated again at least twice, then the filter 3 is once again charged with dust at 700 Pa, for example of ASHRAE type, and the test sequence is repeated at least twice.

Finally, the dust retention capability of the filter 3 is measured by the test derived from the standard EN 779.

The loss of charge should be monitored regularly during the test.

It will be noted that the invention which has just been described makes it possible to monitor a filter and determine its salt and dust retention capability in a maritime environment, as a function of the quantity of salt water upstream and downstream of the filter 4, of the quantity of salt recovered upstream of the filter 4.

Thus, for a filter to be efficient, the quantity of salt water recovered upstream of the filter should be greater than the quantity of salt water recovered downstream of the filter, the value of the salt water droplet capability and the salt deposition quantity should be greater than or equal to reference values. It may be noted that there is generally a quantity of water, for example 25% of the initial quantity of water, which does not reach the filter 3.

If two of the three parameters below are correct, the performance of the filter is questionable and the test should be repeated. However, if just one of the three parameters is correct, the filter is considered to have failed.

It will also be noted that the invention is not limited to monitoring filters used in a maritime environment but can be used to monitor any filter.

The invention claimed is:

1. A method for monitoring a filter for an air intake duct of a turbine, the method comprising the steps of:
   subjecting the filter to an incident flow of sprayed salt water; and
   measuring parameters of the flow on either side of the filter, representative of a salt retention capability of the filter,
   wherein the measuring step is performed in a test sequence of at least one monitoring test in which measurement members are moved in a test duct in which the filter is placed, and
   wherein each test comprises measurement of a salt concentration, a number of salt water droplets, and a quantity of water.

2. The method of claim 1, in which three fifteen minute tests are performed, at twenty minute intervals.

3. The method of claim 1, in which four test sequences are performed.

4. The method of claim 3, in which the filter is dried between the test sequences.

5. The method of claim 1, wherein the filter is inclined by ten degrees relative to the horizontal axis.

6. The method of claim 1, wherein the filter is a dry filter charged with dust.

7. The method of claim 6, wherein the test sequence is performed on the dry filter charged with dust.

8. The method as claimed in claim 7, wherein the salt retention capability of the filter is measured.

9. A system for monitoring a filter for an air intake duct in a turbine comprising:
   a means for injecting a flow of sprayed salt water toward the filter; and measurement members arranged on either side of the filter for measuring parameters of the flow, representative of a salt retention capability of the filter, wherein the measurement members are configured to be moved in a test duct in which the filter is placed for at least one monitoring test, and wherein each test comprises measurement of a salt concentration, a number of salt water droplets, and a quantity of water.

10. The monitoring system of claim 9, wherein the measurement members comprise at least one measurement member selected from the group consisting of: a flow meter, a conductivity meter, a photometer, a white light spectrometer, a humidity sensor, a pressure sensor and a particle measurement device.

* * * * *